(12) United States Patent
Katsuragawa (10) Patent No.: US 10,517,774 B2
(45) Date of Patent: Dec. 31, 2019

(54) ABSORBENT ARTICLE

(71) Applicant: UNICHARM CORPORATION, Shikokuchuo-shi, Ehime (JP)

(72) Inventor: Kunihiko Katsuragawa, Kagawa (JP)

(73) Assignee: UNICHARM CORPORATION, Ehime (JP)

( * ) Notice: Subject to any disclaimer, the term of this patent is extended or adjusted under 35 U.S.C. 154(b) by 0 days.

(21) Appl. No.: 16/313,138

(22) PCT Filed: Aug. 30, 2016

(86) PCT No.: PCT/JP2016/075308
§ 371 (c)(1),
(2) Date: Dec. 25, 2018

(87) PCT Pub. No.: WO2017/187652
PCT Pub. Date: Nov. 2, 2017

(65) Prior Publication Data
US 2019/0231610 A1   Aug. 1, 2019

(30) Foreign Application Priority Data
Jul. 29, 2016  (WO) .................. PCT/JP2016/072401

(51) Int. Cl.
*A61F 13/15* (2006.01)
*A61F 13/496* (2006.01)
(Continued)

(52) U.S. Cl.
CPC ........ *A61F 13/496* (2013.01); *A61F 13/4902* (2013.01); *A61F 13/49011* (2013.01);
(Continued)

(58) Field of Classification Search
CPC .............. A61F 13/496; A61F 13/49011; A61F 13/49019; A61F 2013/15422; A61F 2013/49034; A61F 2013/4905
See application file for complete search history.

(56) References Cited

U.S. PATENT DOCUMENTS

| 4,840,829 A | 6/1989 | Suzuki et al. |
| 2010/0076390 A1* | 3/2010 | Norrby ............... A61F 13/4902 604/367 |

FOREIGN PATENT DOCUMENTS

| CN | 1337300 A | 2/2002 |
| CN | 102348550 A | 2/2012 |

(Continued)

OTHER PUBLICATIONS

International Search Report in PCT Application No. PCT/JP2016/075308, dated Oct. 18, 2016, 2pp.
(Continued)

Primary Examiner — Jacqueline F Stephens
(74) Attorney, Agent, or Firm — Hauptman Ham, LLP (57) ABSTRACT

An absorbent article has a longitudinal direction and a lateral direction perpendicular to each other, and includes a waist part along the lateral direction. The waist part includes nonwoven fabric and a plurality of stretchable members. In a state in which the waist part is extended along the lateral direction, an opening is formed in the waist part between stretchable members that are adjacent in the longitudinal direction. A high density region exists longitudinally between the opening and one of the adjacent stretchable members. An external region exists longitudinally between the high density region and another one of the adjacent stretchable members. The high density region has a predetermined lateral length. A density of fibers of the nonwoven fabric in the high density region is larger than in the external (Continued)

region. A part of an edge of the opening includes a portion in which fibers are not fused.

9 Claims, 6 Drawing Sheets

(51) Int. Cl.
  *A61F 13/49* (2006.01)
  *A61F 13/513* (2006.01)
  *A61F 13/515* (2006.01)
(52) U.S. Cl.
  CPC .. *A61F 13/49019* (2013.01); *A61F 13/49061* (2013.01); *A61F 13/513* (2013.01); *A61F 13/515* (2013.01); *A61F 2013/15422* (2013.01); *A61F 2013/4905* (2013.01); *A61F 2013/49034* (2013.01)

(56) References Cited

FOREIGN PATENT DOCUMENTS

| CN | 103750956 A | 4/2014 |
|----|----|----|
| CN | 105307616 A | 2/2016 |
| EP | 0214608 A2 | 3/1987 |
| JP | S63-243360 A | 10/1988 |
| JP | H4-35662 A | 2/1992 |
| JP | H4-58951 A | 2/1992 |
| JP | 2002-178428 A | 6/2002 |
| JP | 2003-116909 A | 4/2003 |
| JP | 2004-267335 A | 9/2004 |
| JP | 2011-78477 A | 4/2011 |
| JP | 2015-107223 A | 6/2015 |
| WO | 99/00082 A1 | 1/1999 |
| WO | WO 03/047488 * | 6/2003 ............. A61F 13/15 |
| WO | 2009/031592 A1 | 3/2009 |

OTHER PUBLICATIONS

International Preliminary Report on Patentability in PCT Application No. PCT/JP2016/075308, dated Oct. 18, 2016, 10pp.
Office Action in CN Application No. 201680086345.0, dated May 30, 2019, 6pp.
Extended European Search Report in EP Application No. 16900522.0, dated Jun. 5, 2019, 9pp.

* cited by examiner

ABSORBENT ARTICLE

RELATED APPLICATIONS

The present application is a National Phase of PCT/JP2016/075308, filed Aug. 30, 2016, and claims priority based on International Patent Application No. PCT/JP2016/072401, filed Jul. 29, 2016.

TECHNICAL FIELD

The present invention relates to an absorbent article.

BACKGROUND ART

Conventional disposable diapers and the like are known as absorbent articles that absorb excrement such as urine. For example, as described in Patent Literature 1, it is known that forming sub-openings in a front part of a pull-on disposable diaper enables a user to pull up the pull-on diaper to wear it by hooking his/her fingers some of the sub-openings and that the sub-openings improves air permeability of the diaper. The sub-openings are formed by cutting out, welding, and slitting.

CITATION LIST

Patent Literature

[Patent Literature 1] Japanese Unexamined Patent Application Publication No. 2004-267335

SUMMARY OF INVENTION

Technical Problem

However, in a disposable diaper described in Patent Literature 1, waist stretchable members are cut to form the sub-openings, and this worsens shrinking force with which the diaper will fit wearer's waist. If the sub-openings are formed by cutting out or slitting, sub-openings shrink in the lateral direction before the disposable diaper is worn because of shrinkage of stretchable members; that is, it is difficult for a user to recognize the presence of the sub-openings. If the sub-opening is formed by welding, the vicinity of each sub-opening is hard. Accordingly, there is a possibility that, when putting a diaper on a user, hard edges of sub-openings come into contact with wearer's skin to feel the wearer uncomfortable.

The present invention has been made in view of conventional problems such as that described above and objectives thereof are to improve air permeability of an absorbent article, to make it easier to recognize the improvement of air permeability, and to improve the touch of a diaper when it is worn.

Solution to Problem

An aspect of the invention to achieve the above advantage is an absorbent article, having a longitudinal direction and a lateral direction perpendicular to each other,
the absorbent article including:
a waist part along the lateral direction,
the waist part including:
nonwoven fabric; and
a plurality of stretchable members that stretch and contract in the lateral direction,
in a state in which the waist part is extended along the lateral direction,
an opening being formed in the waist part between stretchable members that are adjacent in the longitudinal direction,
a high density region existing longitudinally between the opening and one of the adjacent stretchable members,
an external region existing longitudinally between the high density region and another one of the adjacent stretchable members,
the high density region having a predetermined lateral length,
a density of fibers of the nonwoven fabric in the high density region being higher than a density of fibers of the nonwoven fabric in the external region,
at least a part of an edge of the opening including a no-fused portion in which fibers are not fused.

Other features of the present invention will become apparent from the descriptions in the specification and the drawings.

Advantageous Effects of Invention

According to the present invention, concerning an absorbent article in which openings are formed in its waist part in order to improve air permeability, a high density region makes it easier to keep the shape of the openings even when the absorbent article is extended in the lateral direction or even when its stretchable members are in the original unstretched lengths. This makes it easier to visually recognize the openings and also makes it easier to recognize improvement of air permeability. In addition, providing a no-fused portion to the edge of each opening can further soften the edge of the opening, and therefore it is possible to improve the feel of a diaper when coming into contact with skin.

DESCRIPTION OF EMBODIMENTS

At least the following matters will become apparent from the descriptions in the specification and the accompanying drawings.

An absorbent article, having a longitudinal direction and a lateral direction perpendicular to each other, the absorbent article including:
a waist part along the lateral direction,
the waist part including:
nonwoven fabric; and
a plurality of stretchable members that stretch and contract in the lateral direction,
in a state in which the waist part is extended along the lateral direction,
an opening being formed in the waist part between stretchable members that are adjacent in the longitudinal direction,
a high density region existing longitudinally between the opening and one of the adjacent stretchable members,
an external region existing longitudinally between the high density region and another one of the adjacent stretchable members,
the high density region having a predetermined lateral length,
a density of fibers of the nonwoven fabric in the high density region being higher than a density of fibers of the nonwoven fabric in the external region,
at least a part of an edge of the opening including a no-fused portion in which fibers are not fused.

With such an absorbent article, concerning an absorbent article in which openings are formed in its waist part in order to improve air permeability, a high density region makes it easier to keep the shape of the openings even when the absorbent article is extended in the lateral direction or even when its stretchable members are in the original unstretched lengths. This makes it easier to visually recognize the openings and also makes it easier to recognize improvement of air permeability. In addition, providing a no-fused portion to the edge of each opening can further soften the edge of the opening, and therefore it is possible to improve the feel of diaper when coming into contact with skin.

In such an absorbent article, it is desirable
that a low density region exists on a side closer to the opening with respect to the high density region, and
that a density of fibers of the nonwoven fabric in the low density region is lower than a density of fibers of the nonwoven fabric in the high density region.

With such an absorbent article, the low density region having a lower density of fibers is provided in a region closer to the opening. This makes it possible to further soften the edge of the opening, and it is possible to improve the feel of diaper when coming into contact with skin.

In such an absorbent article, it is desirable that
a density of the fibers in the low density region is lower than a density of the fibers in the external region.

With such an absorbent article, the edge of the opening can be further softened, and it is possible to further improve the feel of diaper when coming into contact with skin.

In such an absorbent article, it is desirable that
a center of the opening is located longitudinally above or below a center between the adjacent stretchable members.

With such an absorbent article, a portion of the opening longitudinally close to the stretchable member is more likely to be affected by the stretchable member, and a portion of the opening longitudinally far away from the stretchable member is less likely to be affected by the stretchable member. This makes it possible to change partially the appearance of the opening, and this makes it easier to visually recognize the opening from various angles.

In such an absorbent article, it is desirable
that the waist part includes a skin-side sheet made of nonwoven fabric and a non-skin-side sheet made of nonwoven fabric,
that the stretchable members are placed between the skin-side sheet and the non-skin-side sheet,
that the skin-side sheet and the non-skin-side sheet includes a plurality of joined portions that join fibers of the nonwoven fabric,
that at least either one of the skin-side sheet and the non-skin-side sheet includes a first region having a predetermined area and a second region having the predetermined area,
that a distance between the first region and the opening is lower than a distance between the second region and the opening, and
that a number of joined portions located in the first region is greater than a number of joined portions located in the second region.

With such an absorbent article, providing a joined portion having a relatively high rigidity at a position closer to the opening makes it possible to reduce the possibility that the opening tears when a force is exerted on the waist part (e.g. when putting the diaper on).

In such an absorbent article, it is desirable that
the joined portion is aligned with a center of the opening in the lateral direction.

With such an absorbent article, it is possible to further reduce the possibility that the opening tears in the lateral direction even when the waist part is extended in the lateral direction.

In such an absorbent article, it is desirable that
a lateral length of the high density region is larger than a lateral length of the opening.

With such an absorbent article, the rigidity of the high density region is relatively large. Accordingly, even when the stretchable members shrink, the high density region makes it easier to keep the shape of the opening, and this makes it easier to visually recognize the opening.

In such an absorbent article, it is desirable that
the high density region has a curved shape projecting toward the other one of the adjacent stretchable members.

With such an absorbent article, the high density region having a curved shape makes it easier to keep the shape of the opening. This makes it easier to visually recognize the opening and also makes it easier to recognize improvement of air permeability.

An absorbent article having a longitudinal direction and a lateral direction perpendicular to each other,
the absorbent article including:
a waist part along the lateral direction,
the waist part including:
nonwoven fabric; and
a plurality of stretchable members that stretch and contract in the lateral direction,
in a state in which the waist part is extended along the lateral direction,
an opening being formed in the waist part between stretchable members that are adjacent in the longitudinal direction,
at least a part of an edge of the opening including a no-fused portion in which fibers of the nonwoven fabric are not fused,
at least a part of an edge of the opening including a fused portion in which the fibers are fused, a center of the opening is located longitudinally above or below a center between the adjacent stretchable members.

With such an absorbent article, the no-fused portion on the edge of the opening can further soften the edge of the opening, and therefore it is possible to improve the feel of diaper when coming into contact with skin. A welded portion on the edge of the opening makes it easier to keep the shape of the opening. A portion of the opening longitudinally close to the stretchable member is more likely to be affected by the stretchable member, and a portion of the opening longitudinally far away from the stretchable member is less likely to be affected by the stretchable member. This makes it possible to change partially the appearance of the opening, and this makes it easier to visually recognize the opening from various angles.

===Disposable diaper according to the Present Embodiment===

<<<Configuration of Disposable Diaper 1>>>

Figure 1:
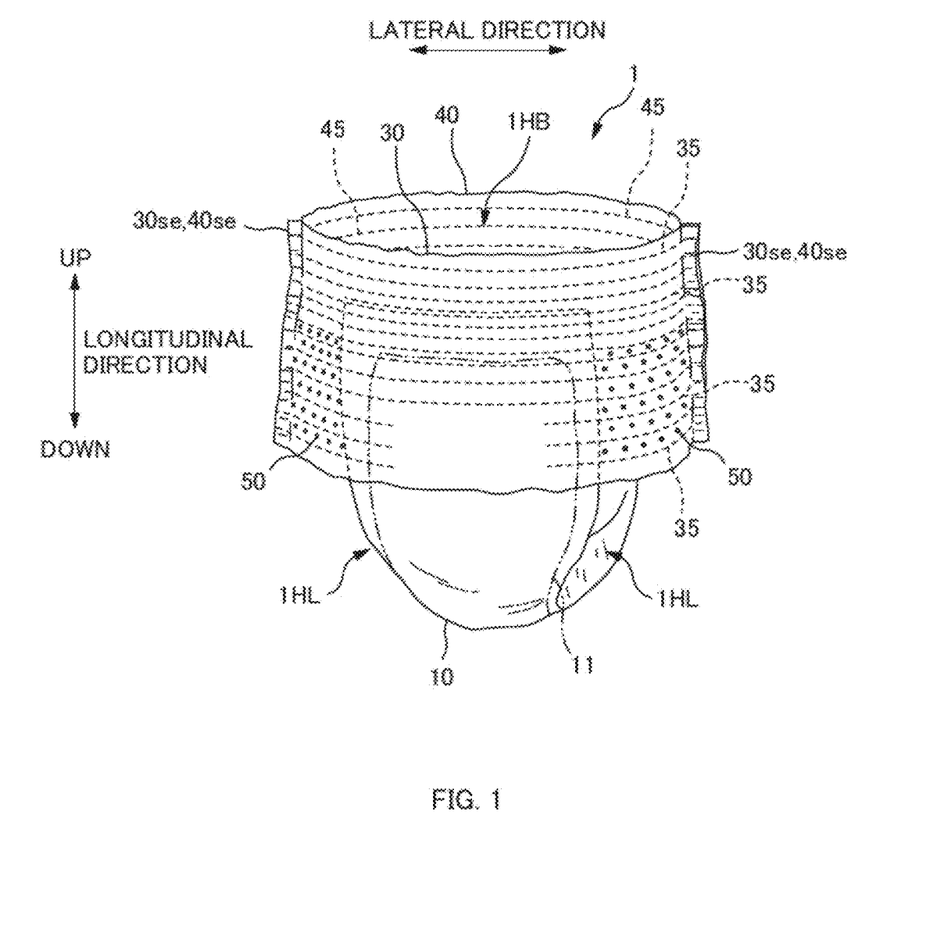
FIG. 1 is a schematic perspective view of a diaper 1, which is an example of an absorbent article according to the present embodiment.
Figure 2:
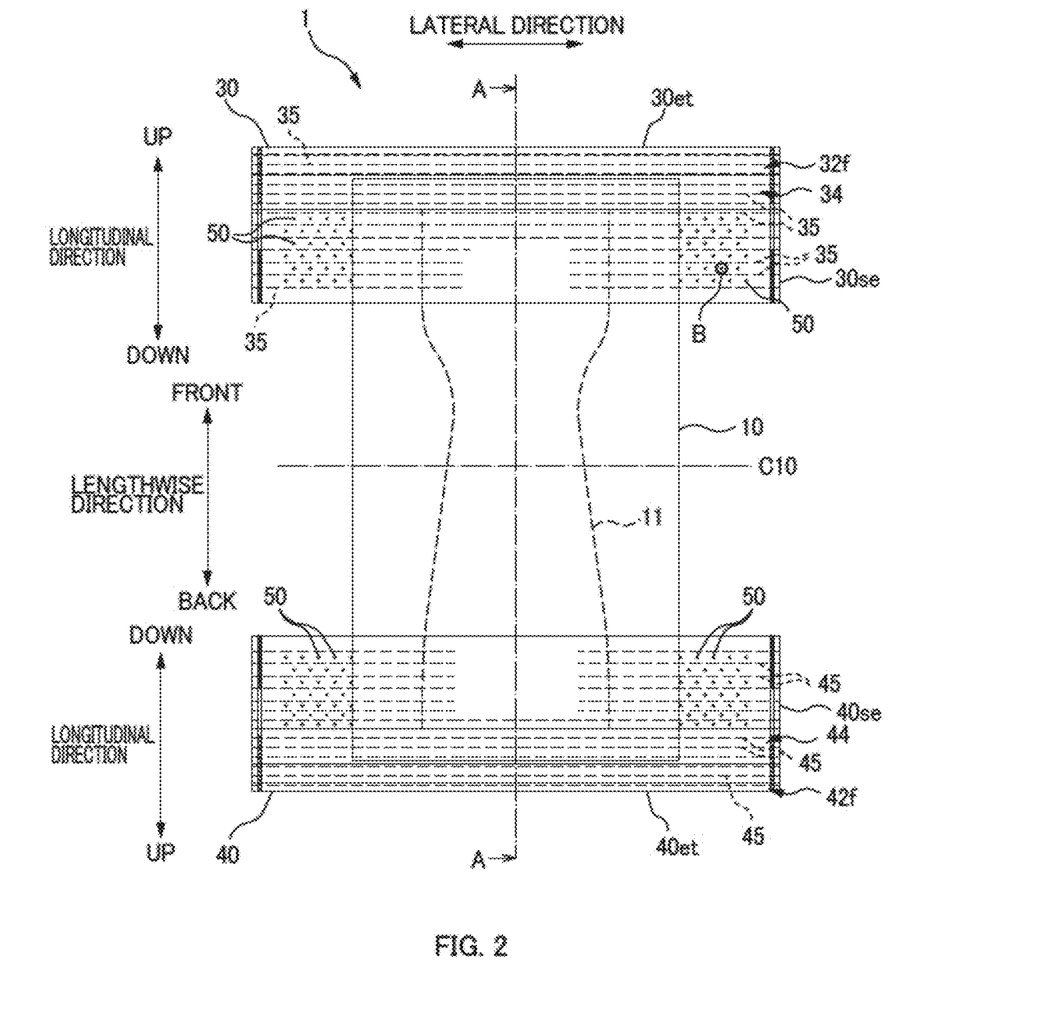
FIG. 2 is a plan view of the diaper 1 which is unfolded and extended as viewed from the skin side.
Figure 3:
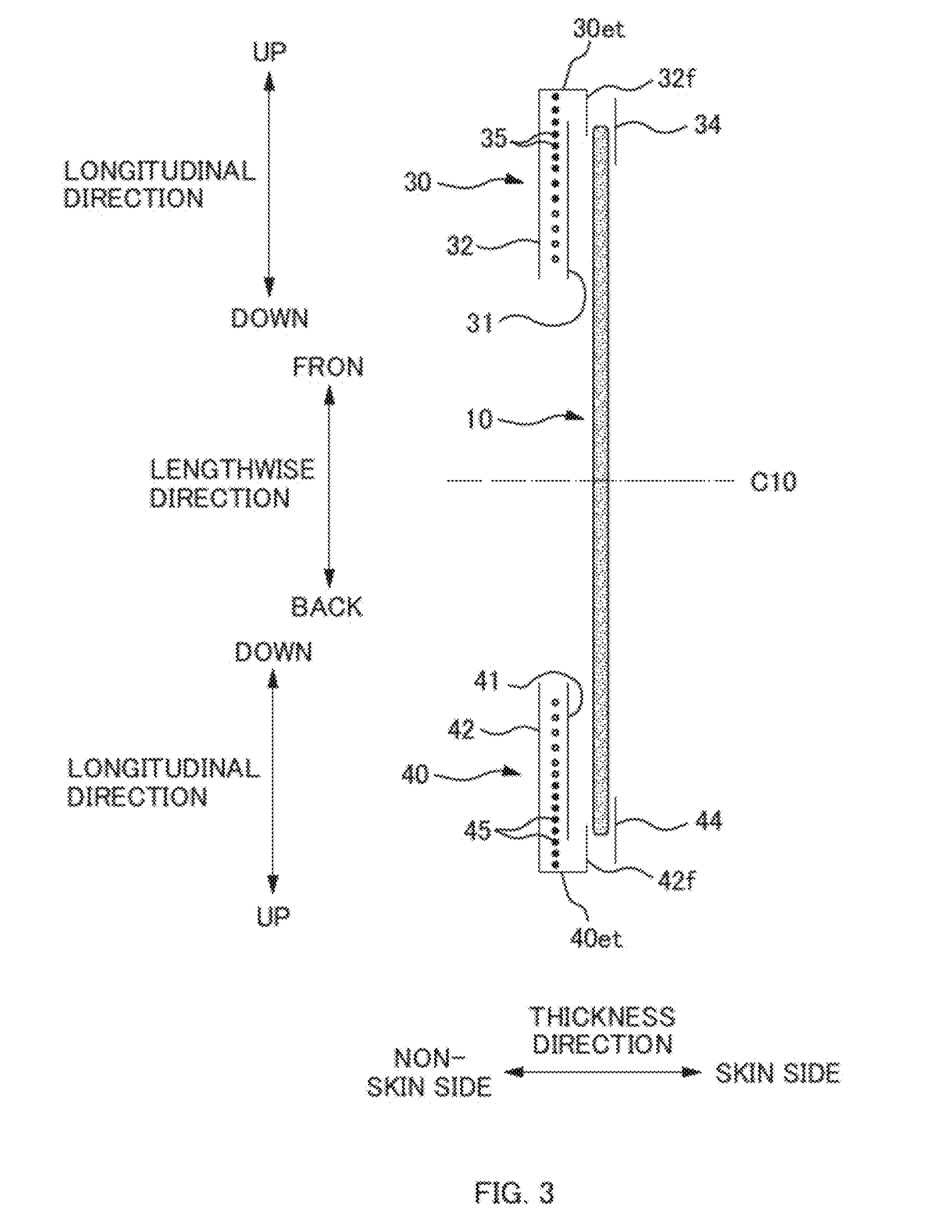
FIG. 3 is a diagram illustrating a cross section of FIG. 2 taken along line A-A.

FIG. 1 is a schematic perspective view of a diaper 1, which is an example of an absorbent article according to the present embodiment. FIG. 2 is a plan view of the diaper 1 which is unfolded and extended as viewed from the skin side. FIG. 3 shows a cross section of FIG. 2 taken along line A-A.

In the description below, when the diaper 1 is worn as shown in FIG. 1, the diaper 1 has a "longitudinal direction", a "lateral direction" that intersects the longitudinal direction, and a "thickness direction" that intersects the longitudinal direction and the lateral direction. A longitudinal side of the diaper 1 closer to the waist opening 1HB is referred to as a "up" side, and a side closer to wearer's crotch is referred to as a "down" side. When the diaper 1 is open as shown in FIG. 2, the lengthwise direction of the diaper 1 is referred to as the "longitudinal direction". And, one side in the lengthwise direction is referred to as a "front" side, and the other side is referred to as a "back" side. A side closer to a substantial lengthwise center C10 is also referred to as "down". In the thickness direction, a side which comes into contact with the wearer is referred to as "skin side", and the opposite side thereof is referred to as a "non-skin side". The line A-A in FIG. 2 and the like indicates the lateral center. An "extended state" or "a state in which a waist part (a front part 30 and a back part 40) is laterally extended" indicate a state in which a diaper 1 (the front part 30 and the back part 40) is extended until its creases disappear. Specifically speaking, the diaper 1 is extended until the lengths of components of the diaper 1 (the front part 30 and the back part 40) become substantially equal to the actual sizes of the components.

A disposable diaper 1 (hereinafter referred to as a "diaper 1") associated with the present embodiment is a so-called pull-on diaper composed of three pieces and is to be worn mainly by an infant. The diaper 1 includes: an absorbent main body 10 placed on wearer's crotch; the front part 30 which covers wearer's front; and the back part 40 which covers wearer's back. The front part 30 and the back part 40 also serve as a waist part which covers wearer's waist.

In open state of FIG. 2, the absorbent main body 10 spans the front part 30 and the back part 40 so that lengthwise ends are placed on the front part 30 and the back part 40. The absorbent main body 10 is joined and fixed to the front part 30 and the back part 40 from the skin side with adhesive or the like. Then, the absorbent main body 10 is placed on the lateral center of the front part 30 and the lateral center of the back part 40. The appearance is a substantially H shape when viewed from above. Folding the set of components at a folding position (the substantial lengthwise center C10) makes the front part 30 and the back part 40 face each other. At a front-part side edge 30se and a back-part side edge 40se, which are lateral edges of the front part 30 and the back part 40, the set of components are joined and connected to become a diaper 1 having a waist opening 1HB and a pair of leg openings 1HL formed therein (FIG. 1).

As shown in FIGS. 2 and 3, the absorbent main body 10 includes: an absorbent body 11; a top-sheet member (not shown) that covers the absorbent body 11 from the skin side; and a back-sheet member (not shown) that covers the absorbent body 11 from the non-skin side. The top-sheet member is a liquid-permeable sheet member such as non-woven fabric. The back-sheet member is a two-layered sheet member composed of a liquid-impermeable leak-proof sheet (e.g. polyethylene) and a liquid-permeable exterior sheet (e.g. nonwoven fabric). The exterior sheet, etc. may form barrier cuffs and leg gathers (not shown).

The absorbent body 11 is an absorbent core made by depositing liquid absorbent material, and can absorb excrement such as urine. The absorbent body 11 may be made of liquid absorbent fiber (pulp fiber), absorbent polymer (SAP) or the like. In the present embodiment, the absorbent body 11 has a substantially sandglass shape as seen from above (FIG. 2). The absorbent body 11 may be covered a liquid-permeable sheet (not shown) such as tissue paper.

The front part 30 and the back part 40 are sheet members having a substantially rectangular shape when seen from above, and are made of nonwoven fabric such as spun-bonded nonwoven fabric, SMS (spun-bonded nonwoven fabric/melt-blown nonwoven fabric/spun-bonded nonwoven fabric) or the like. In the present embodiment, both of spun-bonded nonwoven fabric and SMS nonwoven fabric are used. The spun-bonded nonwoven fabric may be composed of single fiber made of thermoplastic resin (e.g. polypropylene (PP) and polyethylene (PE)) or composite fiber with a core sheath structure made of PP and PE. As shown in FIG. 3, in the front part 30, the skin-side sheet 31 and the non-skin-side sheet 32 are stacked and joined in this order from the skin side in the thickness direction. In the back part 40, the skin-side sheet 41 and the non-skin-side sheet 42 are stacked and joined in this order from the skin side in the thickness direction.

The skin-side sheets 31 and 41 and the non-skin-side sheets 32 and 42 are made by thermal-welding a plurality of PP fibers or other material fibers (long fibers), which constitute nonwoven fabric. A plurality of joined portions (joined portions 3b (FIG. 5)) are formed by compression at certain intervals, and thereby fibers of nonwoven fabric are fixed. In the present embodiment, the skin-side sheets 31 and 41 are made of SMS nonwoven fabric, and the non-skin-side sheets 32 and 42 are made of spun-bonded nonwoven fabric.

As shown in FIG. 3, for the purpose of improvement of touch and durability in the upper end part of the front part 30, the non-skin-side sheet 32 is folded downward on the skin side from an front upper end 30et, to forma folded part 32f; the front upper end 30et is the upper end of the front part 30. Similarly, in the upper part of the back part 40, the non-skin-side sheet 42 is folded downward on the skin side from a back upper end 40et, to forma folded part 42f; the back upper end 40et is the upper end of the back part 40.

The front part 30 includes a sheet member 34 that is placed so as to cover, on the skin side, the lower end part of the folded part 32f and the front upper end part of the absorbent main body 10. Similarly, the back part 40 includes a sheet 44 that is placed so as to cover, on the skin side, the back upper end part of the absorbent main body 10 from below the folded part 42f. The sheet members 34 and 44 are rectangular sheet members made of nonwoven fabric different from those of the front part 30 and the back part 40. Providing the sheet members 34 and 44 enables to prevent wearer's skin from coming into direct contact with the front upper edge or the back upper edge of the absorbent main body 10; therefore, this can make touch around wearer's waist more comfortable. The sheet members 34 and 44 also increase the strength of the upper end parts of the front part 30 and the back part 40.

The front part 30 and the back part 40 have a plurality of openings 50 which are substantially circular through holes extending through the exterior members 30 and 40 respectively from the skin side to the non-skin side. The openings 50 are placed at certain longitudinal and lateral intervals. The details of the opening 50 will be described later.

Between the skin-side sheet 31 and the non-skin-side sheet 32 of the front part 30, a plurality of stretchable members 35 made of elastic string or the like, are placed along the lateral direction. Each stretchable member 35 is joined and fixed with adhesive, etc. to the skin-side sheet 31 and the non-skin-side sheet 32 while extending in the lateral direction. The plurality of stretchable members 35 are lined at longitudinal intervals.

Similarly, between the skin-side sheet 41 and the non-skin-side sheet 42 of the back part 40, a plurality of stretchable members 45 made of elastic string or the like, are placed along the lateral direction. Each stretchable member 45 is joined and fixed with adhesive, etc. to the skin-side sheet 41 and the non-skin-side sheet 42 while extending in the lateral direction. The plurality of stretchable members 45 are lined at longitudinal intervals.

The stretchable members 35 and 45 provide the front part 30 and the back part 40 with stretchability in the lateral direction, and thereby a plurality of creases are generated in the front part 30 and the back part 40. Most of creases on the front part 30 and the back part 40 have shapes along the longitudinal direction.

The stretchable members 35 and 45 discontinue within a region which is near lateral center and overlaps the absorbent body 11, and this prevents stretching force of the stretchable members 35 and 45 from being exerted in the region. Accordingly, lateral shrinkage which acts on the absorbent body 11 is suppressed, and the absorbent body 11 becomes likely to remain substantially flat. This makes it possible to prevent leakage of excretion, or the like.

<<<Opening 50>>>

The opening 50 will be described below. As shown in FIG. 2, each opening 50 of the front part 30 is disposed between stretchable members 35 adjacent in the longitudinal direction. And, each opening 50 of the back part 40 is disposed between stretchable members 45 adjacent in the longitudinal direction. The openings 50 do not cut the stretchable members 35 and 45; that is, the opening 50 do not make the stretchable members 35 and 45 discontinued.

As shown in FIG. 2, the openings 50 of the front part 30 are arranged in a zigzag pattern in a region which does not include the folded part 32f, the sheet member 34 and the absorbent main body 10 and which longitudinally overlaps the absorbent body 11. Similarly, the openings 50 of the back part 40 are arranged in a zigzag pattern in a region which does not include the folded part 42f, the sheet member 44 and the absorbent main body 10 and which longitudinally overlaps the absorbent body 11.

Figure 4A:
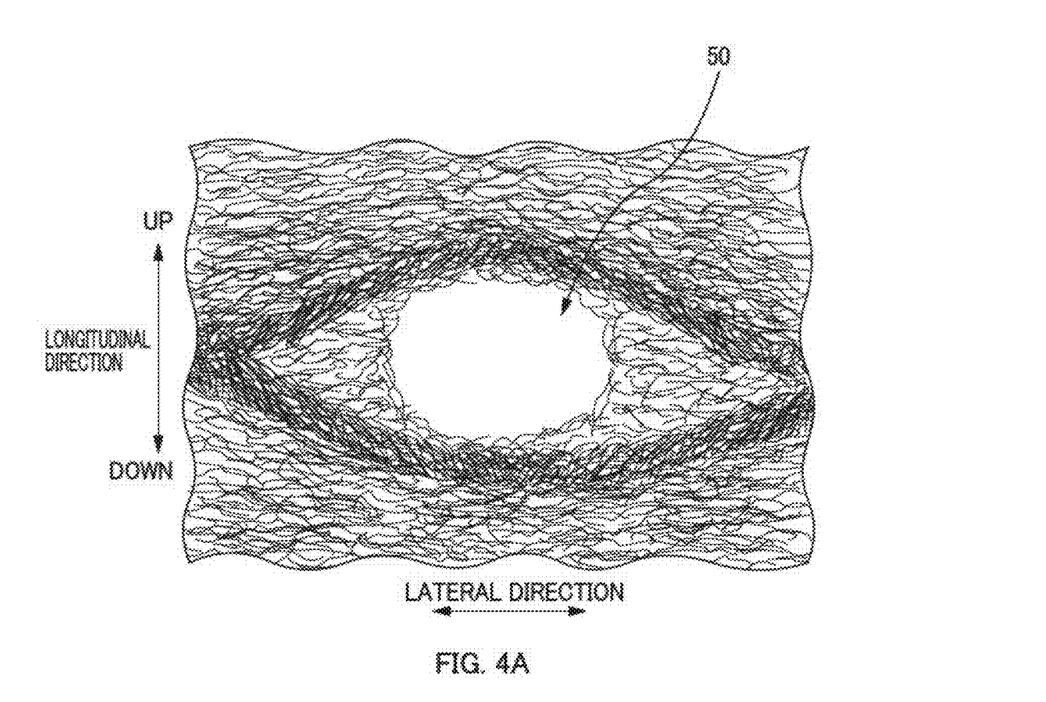
FIG. 4A is a magnified view of an opening 50 in a region B of FIG. 2.
Figure 4B:
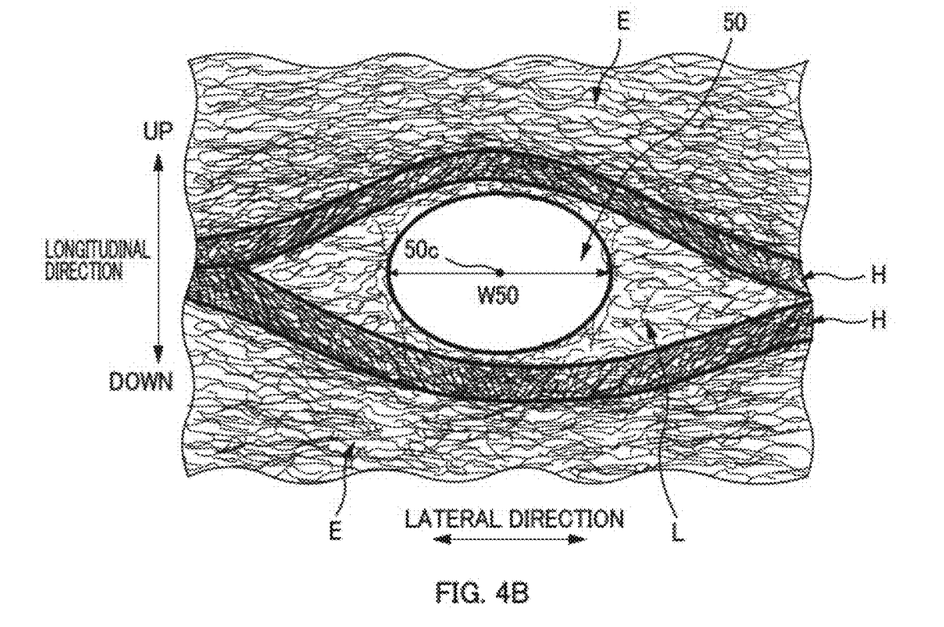
FIG. 4B is a diagram explaining FIG. 4A.
Figure 5:
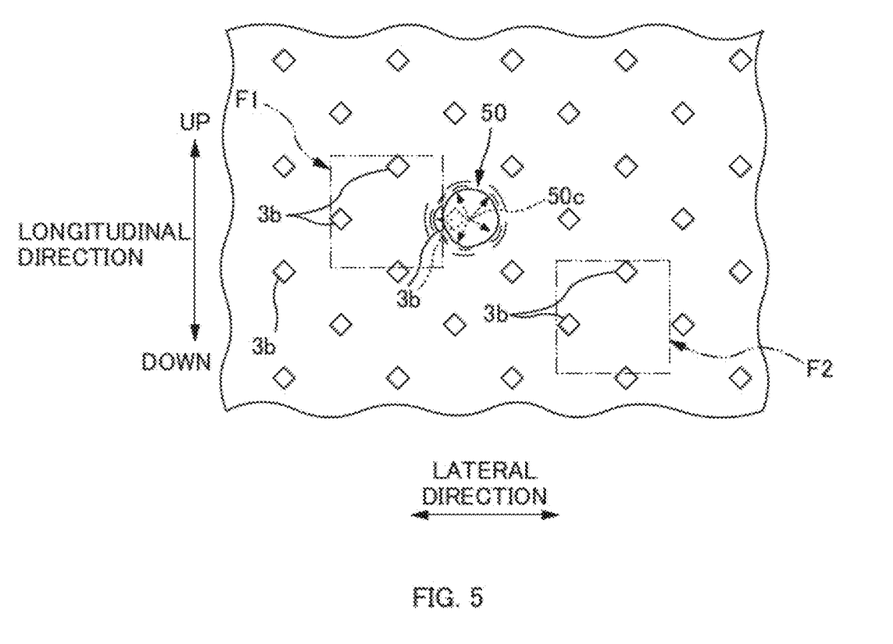
FIG. 5 is a diagram illustrating the opening 50 and joined portions 3b.

FIG. 4A is a magnified view of the opening 50 in the region B of FIG. 2. FIG. 4B is a diagram explaining FIG. 4A. FIG. 5 is a diagram illustrating the opening 50 and the joined portions 3b. FIGS. 4A and 4B are magnified views of the opening 50 when the diaper 1 is extended. FIGS. 4A, 4B and 5 are explanation diagrams with magnified views of one opening 50 of the front part 30, and the same is applied to the openings 50 of the back part 40.

The openings 50 are formed during a process for making the front part 30. In the present embodiment, a bandlike skin-side sheet, continuous stretchable members and a bandlike non-skin-side sheet are stacked sequentially from the skin side. Then, the plurality of the openings 50 are formed at predetermined positions on the bandlike front part (not shown) which has been joined and fixed with adhesive or the like. These are separated to form the front part 30.

The openings 50 are formed as follow: rotating a first rotating body (not shown) including a plurality of pins; simultaneously rotating to the opposite direction a second rotating body (not shown) including a plurality of holes into which the pins are fitted; pushing the pins of the first rotating body through the bandlike front part; and fitting the pins into the holes of the second rotating body. The first rotating body and the second rotating body have built-in heat sources respectively, and these rotating bodies form the openings 50 while heating the bandlike front part. Since the front part 30 is composed of soft fibers made of nonwoven fabric (spun-bonded nonwoven fabric and SMS nonwoven fabric), fitting the pins into the holes is insufficient to keep the openings 50; that is, fibers restore their original shapes so as to close the openings 50. However, heating the bandlike front part at the same time of forming the openings 50 makes it easier to keep the contours of the edges of the openings 50. The first rotating body and the second rotating body heat the nonwoven fabric to a temperature lower than the melting point of the nonwoven fabric. This prevents fibers of the nonwoven fabric from being completely fused and prevents parts of the edges of the openings 50 from hardening; consequently, the edges of the openings 50 has no-fused portion, as shown in FIGS. 4A and 4B. In the present embodiment, the first rotating body and the second rotating body each heat the bandlike front part at a temperature of 80-100° C. The temperature at which the bandlike front part is heated depends on the heat sources and/or the temperature of the first rotating body and the second rotating body or the speed of transporting the bandlike front part.

The openings 50 of the front part 30 formed in the foregoing process have substantially circular shapes of the centers 50c with which pins of the first rotating body had been in contact, as shown in FIG. 4A, when the diaper is extended. But, depending on the material of the nonwoven fabric and/or stretching of the stretchable members 35, the shapes of the openings 50 are substantially ellipses or substantially perfect circles. At this stage, the front member 30 has the openings 50 extending through from the skin side to the non-skin side, the low density regions L around the openings 50, the high density regions H outside the low density region L, and the external region E outside the high density regions. FIG. 4B is a diagram illustrating with projection lines the opening 50 and the surrounding regions of FIG. 4A.

Each opening 50 includes not only a region where the opening 50 penetrates from the skin side to the non-skin side and where no fiber of the nonwoven fabric exists, but also a region where fibers exist in some degrees and where the density of the fibers is equal to or less than the density of the fibers in the external region E. In FIGS. 4A and 4B, fibers within the opening 50 are omitted for the purpose of explanation.

The high density regions H are regions outside the openings 50, and there the density of the fibers of the nonwoven fabric increases because the fibers of the nonwoven fabric are partially extended by pushing pins of the first rotating body into the openings 50. As shown in FIG. 4A, when the openings 50 are formed by pushing pins, substantially-lateral fibers of the nonwoven fabric of the front part 30 form a shape along the contour of an ellipse in which the high density regions H are elongated laterally. That is, the high density region H located above the center 50c of the opening 50 has a curved shape projecting toward the upper stretchable member 35, and the high density region H located below the center 50c of the opening 50 has a curved shape projecting toward the lower stretchable member 35. The high density regions H have more creases than other regions have. The lateral length of each high density region H is larger than the lateral length W50 of the opening 50. The density of fibers of the nonwoven fabric in the high density region H is greater than that of the nonwoven fabric in the external region E, 1.4 to 1.8 times as the density of fibers of the nonwoven fabric in the external region E. In the present embodiment, the density of fibers of the nonwoven fabric in the external region E is approximately 47.5 kg/m$^3$, and the density of fibers of the nonwoven fabric in the high density region H is approximately 75.9 kg/m$^3$.

The low density region L is a region outside the openings 50, and is located inside the high density regions H on a side closer to the openings 50. In each low density region L, the density of fibers of the nonwoven fabric is higher than that in the opening 50 and is lower than that in the external region E. In the present embodiment, the density of fibers of the nonwoven fabric in the low density region L is higher than approximately 4.75 kg/m$^3$ (one tenth of the density of fibers of the nonwoven fabric in the external region E) and is lower than 47.5 kg/m$^3$.

The external region E is a region outside the high density regions H, and located between the high density region H and a stretchable member 35 longitudinally adjacent to the opening 50. The density of fibers of the nonwoven fabric in the external region E is as high as that of the bandlike front part before forming the openings 30. In the external region E, the density of fibers of the nonwoven fabric is lower than that in the high density regions H and is higher than that in the low density regions L.

As a result of forming the opening 50 by pushing pins, a joined portion 3b fixing fibers of nonwoven fabric is pushed out to a position outside the opening 50, as shown in FIG. 5. FIG. 5 is a diagram viewed from a side of the skin-side sheet 31 of the front part 30. A plurality of joined portions 3b formed on nonwoven fabric (the skin-side sheet 31, etc.) are portions which have made as follow: a plurality of fibers are shaped by means such as thermal-welding, and then a plurality of portions are compressed to fix a part of the fibers. The more joined portions 3b are made, the greater the strength of the skin-side sheet 31 can become. And, the less joined portions 3b are made, the softer the touch of the skin-side sheet 31 can become. The joined portions 3b according to the present embodiment are each in a substantially rhombus, and are placed in a zigzag pattern at predetermined intervals. But, the arrangement of the joined portions 3b may be changed appropriately depending on the material, touch and strength of the skin-side sheet 31, and also the shape of each joined portion 3b may be an ellipse depending on the same.

In FIG. 5, a joined portion 3b before forming the opening 50 is indicated by dotted lines. The joined portion 3b before forming the opening 50 is located inside the opening 50; and as a result of forming the opening 50, the joined portion 3b is pushed out laterally outward (leftward in FIG. 5). In a first region F1 having a predetermined area, the number of joined portions 3b is approximately three (equal to or more than three and fewer than four) because there is the joined portion 3b which has been pushed laterally outward. In a second region F2 (rightward below the opening 50 in FIG. 5) having the same area as that of the first region F1 (the predetermined area) and being located farther away from the opening 50 than the first region F1 is, the number of joined portions 3b is approximately two (equal to or more than two and fewer than three). That is, the first region F1 has more joined portions 3b than the second region F2 has. As shown in FIG. 5, one of the joined portions 3b is aligned with the center of the opening 50 in the lateral direction.

<<<Effectiveness of Diaper 1 according to the Present Embodiment>>>

A conventional method to improve air permeability of disposable diapers is forming through holes by cutting a part of its front part or back part. In such a disposable diaper, the front part and the back part shrink in the lateral direction when stretchable members of the front part or of the back part shrink (e.g. before putting the diaper on). This causes the through holes formed by cutting to shrink in the lateral direction; therefore, it is difficult to visually recognize the through holes, and there is a possibility that improved air permeability of the disposable diaper is not recognized.

In a diaper 1 according to the present embodiment, when a front part 30 and a back part 40 are extended along the lateral direction, the front part 30 has openings 50 formed therein between stretchable members 35 adjacent in the longitudinal direction, and the back part 40 has openings 50 formed therein between stretchable members 45 adjacent in the longitudinal direction. A high density region H exists longitudinally between the opening 50 and one of the adjacent stretchable members 35 (45). An external region E exists between high density regions H. The high density region H has a predetermined lateral length. In the high density region H of the front part 30, the density of fibers of the nonwoven fabric is higher than that in the external region E. Thus, in a diaper 1 according to the present embodiment, for the purpose of improving its air permeability, the high density region H is formed between each opening 50 and its adjacent stretchable member 35 (45) when the opening 50 is formed in the front part 30 and the back part 40, which constitute the waist part. That is, between the opening 50 and a stretchable member 35 adjacent thereto in the longitudinal direction, the high density region H and the external region E exist in this order from the opening 50. Accordingly, even when the waist part of a diaper 1 (the back part 30 and the front part 40) shrinks along the lateral direction (e.g. before putting the diaper 1 on), the density of fibers of the nonwoven fabric in the high density region H is high and the rigidity in the high density region H is also large. This makes it easier to keep the shape of the high density region H. Therefore, concerning the opening 50 located inside the high density region H, it becomes easier to keep its shape. This makes it easier to visually recognize the opening 50, and also makes it easier to recognize improvement of air permeability.

Since the opening 50 are formed by pushing pins while heating the front part 30 (the back part 40) as mentioned above, a possibility of fusing fibers of nonwoven fabric increases as the temperature at which nonwoven fabric is heated becomes higher. If fibers of nonwoven fabric are fused, soft fibers harden. Accordingly, the edge of the opening 50 hardens, and therefore there is a possibility that touch of the diaper when coming into contact with skin deteriorates.

Regarding this point, in a diaper 1 according to the present embodiment, a no-fused portion in which fibers are not fused is included on the edge of each opening 50. That is, the opening 50 shown in FIG. 4A in not surrounded by only a region in which fibers are fused, and on the edge of the opening 50, there are some soft fibers that have not been fused. This makes it possible to soften the edge of the opening, and therefore it is possible to improve the feel of diaper when coming into contact with skin.

Note that it is not necessary to provide the no-fused portion throughout the entirety of the edge of the opening 50. Providing a no-fused portion in at least a part of the edge of each opening 50 makes it possible to improve the feel of diaper when coming into contact with skin. However, the edge of the opening can be further softened as the number of no-fused portions provided in the edge of the opening 50 increases.

In a diaper 1 according to the present embodiment, there is the low density region L located on the side closer to the opening 50 with respect to the high density regions H. In the low density region L, the density of fibers of nonwoven fabric is lower than that in the high density regions H. The density of fibers in the low density region L is lower than that in the external region E. The low the density of fibers of the nonwoven fabric is, the softer feel the fibers of the nonwoven fabric have. The low density region L having a lower density of fibers of the nonwoven fabric is provided in a region closer to the opening 50, and this makes it possible to further soften the edge of the opening 50. Accordingly, it is possible to improve the feel of diaper when coming into contact with skin.

In a diaper 1 according to the present embodiment, the front part 30 (the back part 40) includes the skin-side sheet 31 (41) made of nonwoven fabric and the non-skin-side sheet 32 (42) made of nonwoven fabric. Between the skin-side sheet 31 (41) and the non-skin-side sheet 32 (42), the stretchable members 35 (45) are placed. The skin-side sheet 31 (41) and the non-skin-side sheet 32 (42) include a plurality of joined portions 3b that joins fibers of nonwoven fabric. The skin-side sheet 31 (41) and the non-skin-side sheet 32 (42) include the first region F1 having a predetermined area and the second region F2 having the predetermined area. The distance between the first region F1 and the opening 50 is lower than the distance between the second region F2 and the opening 50. The number of joined portions 3b located in the first region F1 is greater than the number of joined portions 3b located in the second region F2. That is, since a joined portion 3b has been pushed out as a result of forming the opening 50 as shown in FIG. 5, the first region F1 near the opening 50 has more joined portions 3b than the second region F2 has. In nonwoven fabric, each joined portion 3b is a portion having a relatively large rigidity and a portion in which fibers of nonwoven fabric are fixed more firmly. Accordingly, it is possible to reduce the possibility that the opening 50 tears when a force is exerted on the front part 30 (e.g. when putting the diaper 1 on).

In a diaper 1 according to the present embodiment, a joined portion 3b is aligned with the center of the opening 50 in the lateral direction. As shown in FIG. 5, a lateral outermost portion of the opening 50 is the longitudinal center of the opening 50. The longitudinal center of the opening 50 is a portion that is most likely to tear when the front part 30 (the back part 40) is extended in the lateral direction. Regarding this, aligning a joined portion 3b with the center of the opening 50 in the lateral direction reduces the possibility that the opening 50 tears in the lateral direction even when the diaper 1 is extended in the lateral direction.

In a diaper 1 according to the present embodiment, the lateral length of the high density region H is larger than the lateral length of the opening 50. As shown in FIG. 4B, the lateral lengths of the high density regions H is larger than the lateral length W50 of the opening 50. Each high density region H has a relatively large rigidity. Accordingly, if the lateral length W50 of the opening 50 is larger than the lateral lengths of the high density region H, the entire region of the opening 50 can be covered with the high density regions H as viewed in the longitudinal direction. Consequently, the high density regions H make it easier to keep the shape of the opening 50, and this makes it easier to visually recognize the opening 50.

In a diaper 1 according to the present embodiment, each high density region H has a curved shape projecting toward one of the stretchable members. That is, as shown in FIGS. 4A and 4B, the high density region H located above the center 50c of the opening 50 has a curved shape projecting toward the upper stretchable member 35, and the high density region H located below the center 50c has a curved shape projecting toward the lower stretchable member 35. The curved shape is a shape extending along the contour of the opening 50. The curved high density region H makes it easier to keep the shape of the opening 50. This makes it easier to visually recognize the opening 50, and also makes it easier to recognize improvement of air permeability.

Figure 6A:
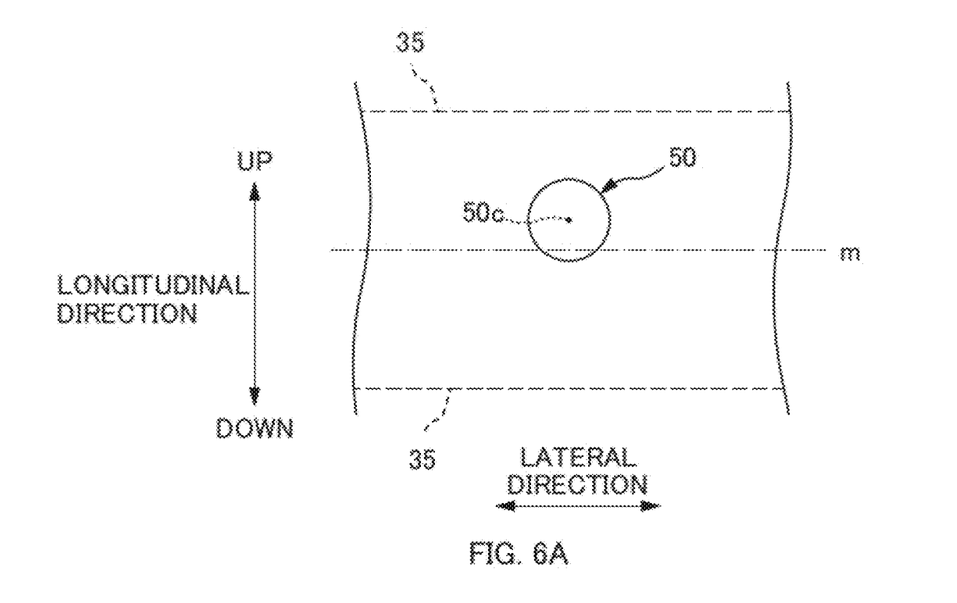
FIG. 6A is a diagram showing a case in which the opening 50 is located above the center between adjacent stretchable members 35.
Figure 6B:
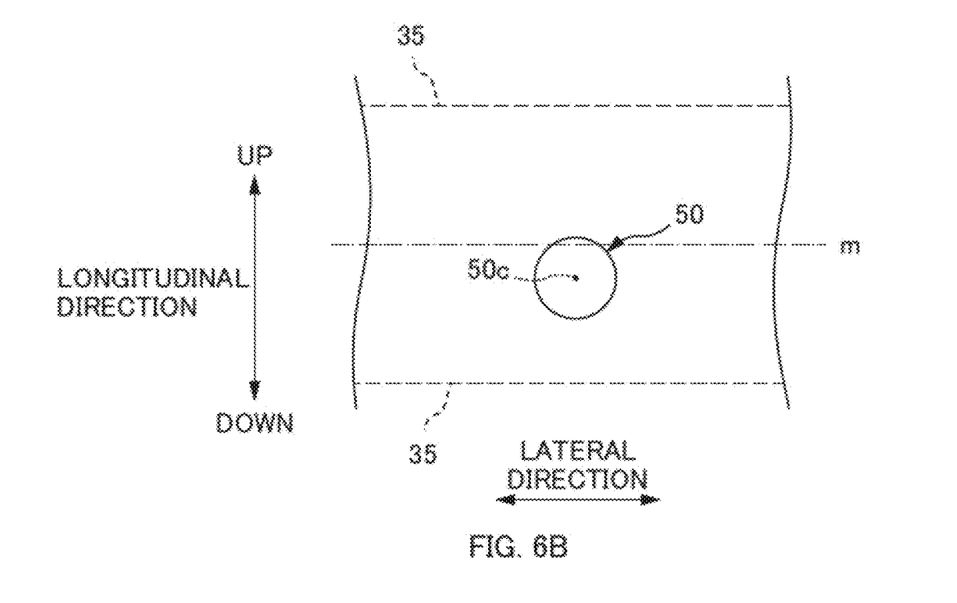
FIG. 6B is a diagram showing a case in which the opening 50 is located below the center between adjacent stretchable members 35.

In the diaper 1, the center of each opening 50 may be located longitudinally above or below the center between adjacent stretchable members. FIG. 6A is a diagram showing a case in which the opening 50 is located above the center between adjacent stretchable members 35. FIG. 6B is a diagram showing a case in which the opening 50 is located below the center between adjacent stretchable members 35. In FIGS. 6A and 6B, an opening 50 of the front part 30 of an extended diaper 1 is illustrated as a simplified circle, and a straight line m indicates the center between stretchable members 35 adjacent in the longitudinal direction. The opening 50 becomes more likely to be affected by stretch/contract of the stretchable member 35 as the opening 50 becomes longitudinally closer to the stretchable member 35. Accordingly, as the opening 50 becomes closer to the stretchable member 35, the opening 50 becomes more likely to shrink or to be pulled by the stretchable member 35. On the other hand, as the opening 50 becomes farther away from the stretchable member, the opening 50 becomes relatively less likely to be affected by stretch/contract of the stretchable member 35. In FIG. 6A, since the center 50c of the opening 50 is located above the straight line m, the upper portion of the opening 50 is more likely to be affected by the upper stretchable member 35 and the lower portion of the opening 50 is less likely to be affected by the lower stretchable member 35. Similarly, in FIG. 6B, since the center 50c of the opening 50 is located below the straight line m, the lower portion of the opening 50 is more likely to be affected by the lower stretchable member 35 and the upper portion of the opening 50 is less likely to be affected by the upper stretchable member 35. Thus, a force exerted on the opening 50 is different between the upper portion and the lower portion; therefore the level at which the opening 50 is shrunk by the stretchable member 35 is different between the upper portion and the lower portion. For example, in the case of FIG. 6A, the upper portion of the opening 50 is located close to the upper stretchable member 35, and the lower portion of the opening 50 is located far away from the lower stretchable member 35. Accordingly, the upper portion of the opening 50 shrinks more than the lower portion of the opening 50. Whereas the upper portion of the opening 50 slightly shrinks in the lateral direction, the lower portion of the opening 50 shrink less than the upper portion does. The edge of the opening 50 looses toward the front side or the back side with respect to the upper portion, and this makes it easier to visually recognize the opening 50 from different angles.

Other Embodiments

Although embodiments of the present invention have been described above, the above-described embodiment is intended to facilitate the understanding of the present invention, and the present invention is not to be construed as being limited to the embodiment. And it is needless to say that various modifications and improvements can be made to the present invention without departing from the gist thereof, and equivalents thereof fall within the present invention. For example, the following modifications are possible.

In the foregoing embodiment, the openings 50 are formed on both of the front part 30 and the back part 40. However, the present invention is not limited thereto. The openings 50 may be formed on either one of the front part 30 and the back part 40. But, forming the openings 50 on both of the front part 30 and the back part 40 further improves air permeability of the diaper 1.

In the foregoing embodiment, the openings 50 are formed at lower positions than the upper end of the absorbent main body 10; more preferably, the openings 50 are formed at lower positions than the upper end of the absorbent body 11. However, the present invention is not limited thereto. The opening 50 may be formed at upper positions than the upper end of the absorbent body 11 or at upper positions than the absorbent main body 10. Thus, it is possible to appropriately arrange the openings 50 at positions which are more likely to secrete sweat such as abdomen or buttock. But, as in the foregoing embodiment, in a case where the openings 50 are formed at lower positions than the absorbent main body 10, in particular at lower positions than the upper end of the absorbent body 11 makes it possible to reduce a possibility of deterioration in strength of the diaper 1 against a vertical force. In addition, this can improve air permeability of the diaper 1.

In the foregoing embodiment, there is the low density region L located on the side closer to the opening 50 with respect to the high density regions H. However, the present invention is not limited thereto. A region adjacent to the opening 50 may be a high density region H. This makes it easier to keep the shape of the opening 50. In addition to this, the high density region H has more creases; therefore, it is possible to improve the feel of diaper when coming into contact with skin.

In the foregoing embodiment, the skin-side sheets 31 and 41 and the non-skin-side sheets 32 and 42 have the joined portions 3b and the joined portions 4b, which join fibers of nonwoven fabric. However, the present invention is not limited thereto. Nonwoven fabric which is formed by heating and welding fibers, or in which fibers are entangled by hot air or air-through may be employed, that is, nonwoven fabric which does not have a joined portion processed by compression. Without a joined portion, it is possible to make a softer sheet.

In a state in which the front part 30 and the back part 40 are extended along the lateral direction, the openings are formed in the front part 30 between the stretchable members 35 adjacent in the longitudinal direction, and the openings are formed in the back part 40 between the stretchable members 45 adjacent in the longitudinal direction. In addition, at least a part of the edge of each opening 50 includes the no-fused portion in which fibers of nonwoven fabric are not fused, and at least a part of the edge of the opening 50 includes a fused portion in which fibers are fused. The center of each opening 50 may be located longitudinally above or below the center between adjacent stretchable members 35 (45). Accordingly, the no-fused portion on the edge of the opening 50 can further soften the edge of opening, and therefore it is possible to improve the feel of diaper when coming into contact with skin. A welded portion on a part of the edge of opening makes it easier to keep the shape of the opening 50 that has been made by a pin or the like. This improves air permeability, and this also makes it possible to recognize improvement of air permeability from its appearance. A portion of the opening longitudinally close to the stretchable member is more likely to be affected by the stretchable member, and a portion of the opening longitudinally far away from the stretchable member is less likely to be affected by the stretchable member. This makes it possible to change partially the appearance of the opening, and this makes it easier to visually recognize the opening from various angles.

A diaper 1 according to the foregoing embodiment is for use with an infant. However, the present invention is not limited thereto. The diaper 1 may be for use with an adult. In the foregoing embodiment, a so-called three-piece disposable diaper 1 is provided as an example of an absorbent article. However, the present invention is not limited thereto. For example, a two-piece disposable diaper including an exterior sheet composed of a front part, a crotch part and a back part (a first component) and an absorbent main body fixed to the skin-side surface of the exterior sheet (a second component) may be employed, and a type-type disposable diaper may also be employed.

REFERENCE SIGNS LIST 1 diaper (absorbent article), 1HB waist opening, 1HL leg opening, 3b joined portion, 10 absorbent main body, 11 absorbent body, 30 front part (waist part), 30et front upper end, 30se front-part side edge, 31 skin-side sheet, 32 non-skin-side sheet, 32f folded part, 34 sheet member, 35 stretchable member, 40 back part (waist part), 40et back upper end, 40se back-part side edge, 41 skin-side sheet, 42 non-skin-side sheet, 42f folded part, 44 sheet member, 45 stretchable member, 50 opening, 50c center, F1 first region, F2 second region

The invention claimed is:

1. An absorbent article having a longitudinal direction and a lateral direction perpendicular to each other, the absorbent article comprising:
  a waist part along the lateral direction, the waist part including:
    nonwoven fabric having fibers; and
    a plurality of stretchable members that stretch and contract in the lateral direction, wherein
  in a state in which the waist part is extended along the lateral direction, an opening is formed in the waist part between stretchable members that are adjacent in the longitudinal direction,
  the nonwoven fabric of the waist part includes
    a high density region existing longitudinally between the opening and one of the adjacent stretchable members, and an external region existing longitudinally between the high density region and another one of the adjacent stretchable members, the high density region has a predetermined lateral length, a density of the fibers of the nonwoven fabric in the high density region is higher than a density of the fibers of the nonwoven fabric in the external region, and at least a part of an edge of the opening includes a no-fused portion in which the fibers are not fused.

2. An absorbent article according to claim 1, wherein the nonwoven fabric further includes a low density region existing on a side closer to the opening with respect to the high density region, and a density of the fibers of the nonwoven fabric in the low density region is lower than the density of the fibers of the nonwoven fabric in the high density region.

3. An absorbent article according to claim 2, wherein the density of the fibers of the nonwoven fabric in the low density region is lower than the density of the fibers of the nonwoven fabric in the external region.

4. An absorbent article according to claim 1, wherein a center of the opening is located longitudinally above or below a center between the adjacent stretchable members.

5. An absorbent article according to claim 1, wherein the waist part includes a skin-side sheet made of the nonwoven fabric and a non-skin-side sheet made of the nonwoven fabric, the stretchable members are placed between the skin-side sheet and the non-skin-side sheet, the skin-side sheet and the non-skin-side sheet includes a plurality of joined portions that join the fibers of the nonwoven fabric, at least one of the skin-side sheet or the non-skin-side sheet includes a first region having a predetermined area and a second region having the predetermined area, a distance between the first region and the opening is less than a distance between the second region and the opening, and the number of joined portions located in the first region is greater than the number of joined portions located in the second region.

6. An absorbent article according to claim 5, wherein the joined portion is aligned with a center of the opening in the lateral direction.

7. An absorbent article according to claim 1, wherein a lateral length of the high density region is larger than a lateral length of the opening.

8. An absorbent article according to claim 1, wherein the high density region has a curved shape projecting toward the another one of the adjacent stretchable members.

9. An absorbent article having a longitudinal direction and a lateral direction perpendicular to each other, the absorbent article comprising:
  a waist part along the lateral direction,
    the waist part including:
      nonwoven fabric; and
      a plurality of stretchable members that stretch and contract in the lateral direction, in a state in which the waist part is extended along the lateral direction,
  an opening being formed in the waist part between stretchable members that are adjacent in the longitudinal direction,
  at least a part of an edge of the opening including a no-fused portion in which fibers of the nonwoven fabric are not fused,
  at least a part of an edge of the opening including a fused portion in which the fibers are fused,
  a center of the opening being located longitudinally above or below a center between the adjacent stretchable members.

* * * * *